(12) United States Patent
Lee et al.

(10) Patent No.: US 12,280,352 B2
(45) Date of Patent: Apr. 22, 2025

(54) CONTINUOUS STIRRED TANK REACTOR FOR ALDOL CONDENSATION REACTION

(71) Applicant: HANWHA SOLUTIONS CORPORATION, Seoul (KR)

(72) Inventors: Shinbeom Lee, Daejeon (KR); Hyojin Jeon, Daejeon (KR); Gyeongseon Jeong, Daejeon (KR); Keedo Han, Daejeon (KR); Junhee Han, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 284 days.

(21) Appl. No.: 17/767,427

(22) PCT Filed: Aug. 5, 2020

(86) PCT No.: PCT/KR2020/010300
§ 371 (c)(1),
(2) Date: Apr. 7, 2022

(87) PCT Pub. No.: WO2021/071074
PCT Pub. Date: Apr. 15, 2021

(65) Prior Publication Data
US 2024/0100497 A1    Mar. 28, 2024

(30) Foreign Application Priority Data
Oct. 8, 2019 (KR) .................. 10-2019-0124786

(51) Int. Cl.
*B01J 19/00* (2006.01)
*B01D 17/02* (2006.01)
(Continued)

(52) U.S. Cl.
CPC .......... *B01J 19/1862* (2013.01); *B01D 17/02* (2013.01); *B01F 27/0723* (2022.01);
(Continued)

(58) Field of Classification Search
CPC ................ B01J 19/1862; B01J 19/0066; B01J 2219/00033; B01J 2219/0004;
(Continued)

(56) References Cited

U.S. PATENT DOCUMENTS 9,333,468 B2 * 5/2016 Nguyen ............. D21C 11/0007

FOREIGN PATENT DOCUMENTS

| CN | 109563013 A | * 4/2019 | ............. B01J 19/00 |
| FR | 2763867 B1 | 7/1999 | |

(Continued)

OTHER PUBLICATIONS

CN-109563013 A machine translation (Year: 2025).*

(Continued)

*Primary Examiner* — Huy Tram Nguyen
(74) *Attorney, Agent, or Firm* — Harvest IP Law, LLP

(57) ABSTRACT

Provided is a continuous stirred tank reactor for an aldol condensation reaction and an apparatus for an aldol condensation reaction including the same, which prevent a decrease in a conversion rate due to dead zone occurrence even in the case of an increase of an installation scale, have a high output, have a significantly increased reaction surface area during the reaction, suppress layer separation between an aqueous phase and an organic phase, and have a significantly decreased average particle diameter of organic layer particles dispersed in the aqueous phase and a significantly decreased deviation thereof. In addition, a content of the catalyst used per unit yield may be significantly decreased as compared with the conventional reactor and apparatus, and costs required for wastewater treatment may be significantly reduced as compared with the conventional reactor and apparatus.

9 Claims, 2 Drawing Sheets

(51) Int. Cl.
*B01F 27/072* (2022.01)
*B01F 27/191* (2022.01)
*B01F 27/90* (2022.01)
*B01J 19/18* (2006.01)
*C07C 45/45* (2006.01)
*B01F 101/00* (2022.01)

(52) U.S. Cl.
CPC ........ *B01F 27/0726* (2022.01); *B01F 27/191* (2022.01); *B01F 27/90* (2022.01); *B01J 19/0066* (2013.01); *C07C 45/45* (2013.01); *B01F 2101/2204* (2022.01); *B01F 2215/0422* (2013.01); *B01J 2219/00033* (2013.01)

(58) Field of Classification Search
CPC .......... B01J 2219/00779; B01J 19/0013; B01J 19/006; B01J 19/243; B01J 19/18; B01J 8/008; B01J 8/10; B01J 2219/0059; B01J 19/0046; B01J 2219/00479; B01D 17/02; B01F 27/0723; B01F 27/0726; B01F 27/191; B01F 27/90; B01F 2101/2204; B01F 2215/0422; B01F 25/25; B01F 25/53; C07C 45/45; C07C 45/50

USPC ........................................................ 422/618
See application file for complete search history.

(56) References Cited

FOREIGN PATENT DOCUMENTS

| | | |
|---|---|---|
| JP | 2000239218 A | 9/2000 |
| JP | 2012144522 A | 8/2012 |
| KR | 1019980028461 A | 7/1998 |
| KR | 1020060073044 A | 6/2006 |
| KR | 20120032701 A | 4/2012 |
| KR | 20180021646 A | 3/2018 |
| WO | 2018236823 A1 | 12/2018 |

OTHER PUBLICATIONS

An office action issued on Sep. 18, 2023 for corresponding KR Patent Application.
CN office action issued on Mar. 22, 2024.
An European search report issued on Sep. 12, 2023.

* cited by examiner

[FIG. 1]
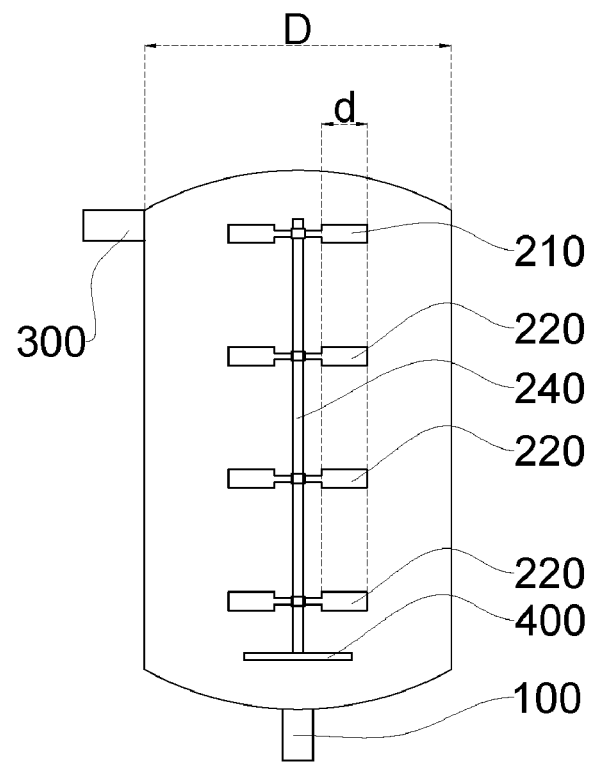
[FIG. 2]
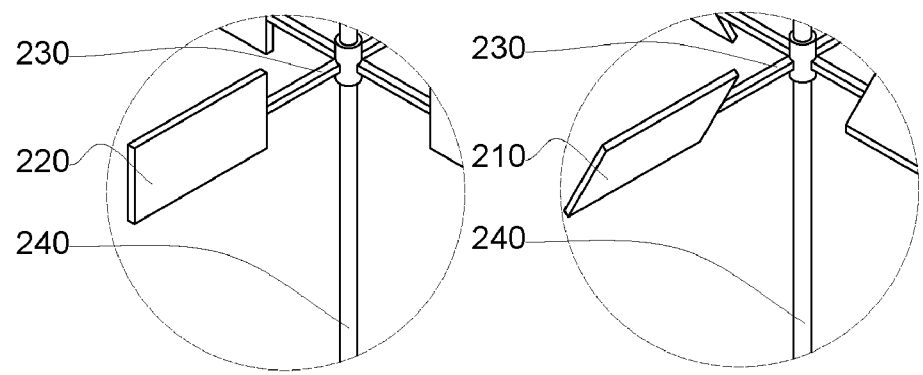

[FIG. 3]
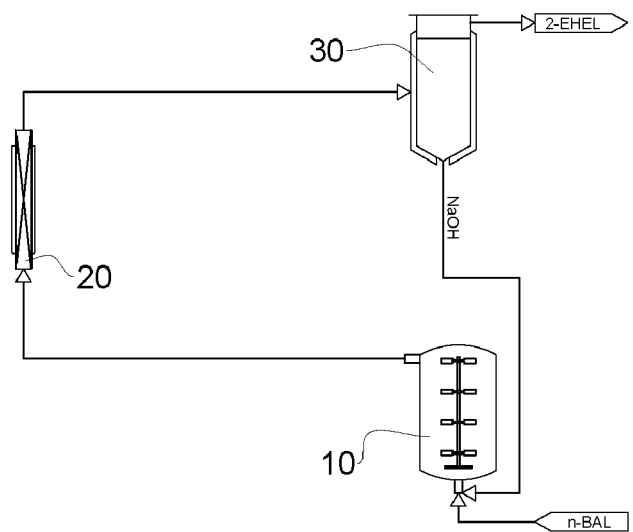

CONTINUOUS STIRRED TANK REACTOR FOR ALDOL CONDENSATION REACTION

CROSS-REFERENCE TO RELATED APPLICATIONS

This application is a National Stage of International Application No. PCT/KR2020/010300 filed Aug. 5, 2020, claiming priority based on Korean Patent Application No. 10-2019-0124786 filed Oct. 8, 2019, the disclosure of which is incorporated herein by reference in its entirety.

TECHNICAL FIELD

The present invention relates to a continuous stirred tank reactor for an aldol condensation reaction.

BACKGROUND ART

In general, an aldol condensation reaction refers to a process in which various olefins and synthetic gas (CO/H2) are reacted by a hydroformylation reaction known as an oxo reaction in the presence of a metal catalyst and a ligand to produce linear and branched aldehydes having one more carbon atoms on the olefin, from which alpha and beta unsaturated aldehydes are produced by an aldol condensation reaction.

The unsaturated aldehyde synthesized after the condensation reaction of an aldol and the like may be converted into various acids and alcohols containing a long alkyl group by an oxidation or reduction reaction, and these alcohols and acids are used as a raw material of solvents, additives, and various plasticizers, and the like.

Korean Patent Laid-Open Publication No. 10-1996-0047519 discloses that in the technology related to a preparation method of neopentyl glycol, an unreacted aldehyde recovery column is provided after an aldol condensation reactor, thereby circulating the unreacted material to improve reaction efficiency. In addition, Korean Patent Laid-Open Publication No. 10-2004-0111873 discloses that in the technology related to a preparation method of neopentyl glycol, the aldol condensation reaction is performed in continuous stirred tank reactors (CSTR) arranged in series as two or more reactors.

However, until now, when using the continuous stirred tank reactor for synthesizing an aldehyde-based compound from an unsaturated aldehyde by the aldol condensation reaction, in particular, when mass production by a production increase is intended, a dead zone which refers to a zone having deteriorated mixing performance has occurred locally in one area inside the reactor. When the dead zone occurs inside the reactor, not only a conversion rate and a yield are lowered, but also reaction efficiency and energy efficiency are decreased, a required conversion rate and a facility scale relative to a yield are increased, and variables due to a difference in a theoretical design and a problem occurrence frequency resulting therefrom are increased to increase uncertainty.

Accordingly, a study of the continuous stirred tank reactor for an aldol condensation reaction which may minimize the dead zone occurring inside the reactor, have high conversion rate and yield, and have excellent reaction efficiency and energy efficiency, is demanded.

DISCLOSURE

Technical Problem

An object of the present invention is to provide a continuous stirred tank reactor for an aldol condensation reaction which prevents a decline in a conversion rate due to occurrence of a dead zone even in the case of an increased facility scale and has high productivity, and an apparatus for an aldol condensation reaction including the same.

Another object of the present invention is to provide a continuous stirred tank reactor for an aldol condensation reaction which significantly increases a reaction surface area during reaction, suppresses layer separation of an aqueous phase and an organic layer, and significantly decreases an average particle diameter of organic layer particles dispersed in the aqueous phase and a deviation thereof, and an apparatus for an aldol condensation reaction including the same.

Still another object of the present invention is to provide a continuous stirred tank reactor for an aldol condensation reaction which may significantly decrease a content of a catalyst used per a unit yield as compared with a conventional reactor and significantly reduce costs required for wastewater treatment as compared with the conventional reactor, and an apparatus for an aldol condensation reaction including the same.

Technical Solution

In one general aspect, a continuous stirred tank reactor for an aldol condensation reaction, which is a reactor having a bottom-up structure in which a reactant flows from a lower portion into an upper portion, includes: a reactant inlet 100 provided in a lower portion of a reactor; a stirring unit 200 including multi-stage paddles spaced apart from each other in a vertical direction, provided in an upper side of the reactant inlet 100; and an outlet 300 provided in an upper side of the stirring unit 200, wherein the multi-stage paddles are a pitched paddle disposed at a top and a plurality of multi-stage flat paddles disposed in a lower end thereof.

In an exemplary embodiment of the present invention, the stirring unit 200 may include a rotating shaft 240 connected to the multi-stage paddles, and the pitched paddle may include a plurality of pitched blades 210 formed in a state of being twisted at an angle of 20 to 70° in a length direction of the rotating shaft 240.

In an exemplary embodiment of the present invention, the stirring unit 200 may include a rotating shaft 240 connected to the multi-stage paddles, and the flat paddle may include a plurality of flat blades 220 formed at an angle of −10 to 10° in a length direction of the rotating shaft 240.

The continuous stirred tank reactor for an aldol condensation reaction according to an exemplary embodiment of the present invention may further include an impingement baffle 400 which is provided in a lower side of a bottom flat paddle among the multi-stage flat paddles and with which a reactant flowing from the inlet 100 collides to be dispersed to an outside of the reactor.

In an exemplary embodiment of the present invention, the paddle may include a support 230 for connecting the pitched blade 210 to the rotating shaft 240, and a ratio between a width (d) of the pitched blade 210 and a width (D) of the inside of the reactor may be 0.2 to 0.4.

In an exemplary embodiment of the present invention, the paddle may include a support 230 for connecting the pitched blade 210 to the rotating shaft 240, and a ratio between a width (d) of the flat blade 220 and a width (D) of the inside of the reactor may be 0.4 to 0.5.

In an exemplary embodiment of the present invention, the stirring unit 200 may disperse the reactant in an aqueous phase at an average particle size of 50 to 500 μm.

In another general aspect, an apparatus for an aldol condensation reaction includes the continuous stirred tank reactor for an aldol condensation reaction.

The apparatus for an aldol condensation reaction according to the present invention may include the continuous stirred tank reactor 10 for an aldol condensation reaction; a plug flow reactor 20 into which a reactant, a catalyst, and a product flow from the continuous stirred tank reactor for an aldol condensation reaction; and an oil-water separator 30 into which the product and the catalyst flow from the plug flow reactor and which separates the catalyst with an aqueous layer and separates the product with an organic layer.

Advantageous Effects

The continuous stirred tank reactor for an aldol condensation reaction and the apparatus for an aldol condensation reaction including the same according to the present invention prevent a decline in a conversion rate due to occurrence of a dead zone even in the case of an increased facility scale and have high productivity.

The continuous stirred tank reactor for an aldol condensation reaction and the apparatus for an aldol condensation reaction including the same according to the present invention have a significantly increased reaction surface area during the reaction, suppress layer separation between an aqueous phase and an organic phase, and have significantly decreased average particle diameter of organic layer particles dispersed in the aqueous phase and deviation thereof.

The continuous stirred tank reactor for an aldol condensation reaction and the apparatus for an aldol condensation reaction including the same according to the present invention have a significantly decreased content of a catalyst used per unit yield as compared with conventional ones and may significantly reduce costs required for wastewater treatment as compared with the conventional ones.

DESCRIPTION OF DRAWINGS

FIG. 1 is a drawing showing a continuous stirred tank reactor for an aldol condensation reaction according to the present invention.

FIG. 2 is a drawing specifically showing a stirring unit provided inside the continuous stirred tank reactor for an aldol condensation reaction according to the present invention.

FIG. 3 is a process flow diagram in which an apparatus for an aldol condensation reaction including the continuous stirred tank reactor for an aldol condensation reaction according to the present invention is schematized.

BEST MODE

Hereinafter, the continuous stirred tank reactor for an aldol condensation reaction according to the present invention will be described in detail with reference to the accompanying drawing.

The drawings illustrated in the present specification are provided by way of example so that the idea of the present invention may be sufficiently conveyed to a person skilled in the art. Therefore, the present invention is not limited to the provided drawings, but may be embodied in many different forms, and the drawings may be exaggerated in order to clear the spirit of the present invention.

Technical terms and scientific terms used in the present specification have the general meaning understood by those skilled in the art to which the present invention pertains unless otherwise defined, and a description for the known function and configuration obscuring the gist of the present invention will be omitted in the following description and the accompanying drawings.

The singular form of the term used herein may be intended to also include a plural form, unless otherwise indicated.

The unit of % used herein without particular mention refers to % by weight, unless otherwise defined.

In a process of synthesizing an unsaturated aldehyde from an aldehyde-based reactant by an aldol condensation reaction, the reactant is reacted by a catalyst in an aqueous phase including the catalyst to synthesize a product which is present in an organic layer, and the reaction is performed in a liquid phase. Up to date, when an aldol condensation reaction system is increased to increase production so that a large-scale facility having a reaction volume of 500 L, specifically 600 L or more is constructed, a dead zone and layer separation locally occur in one area inside the reactor, which causes decreases in a conversion rate and a yield and lowers reaction efficiency and energy efficiency. In addition, a required conversion rate and a facility scale relative to a yield are increased, of course, and variables due to a difference in a theoretical design and a problem occurrence frequency resulting therefrom are increased to increase uncertainty.

Therefore, in order to increase the conversion rate and the yield, it is required to decrease the size of the organic layer particles dispersed in the aqueous phase to increase a reaction surface area and minimize dead zone formation. However, up to date, even in the case in which a rotation speed of an impeller was increased, it was difficult to decrease the size of the organic layer particles and a layer separation phenomenon was rather increased, and also, there was a limitation in minimizing the dead zone.

Thus, in the present invention, a continuous stirred tank reactor having an internal structure having a specific form described later is provided, whereby a mass production system allowing a large amount of products to be produced per unit time may be established, while dead zone formation inside the reactor during the reaction is prevented, the conversion rate and the yield may be significantly improved, and an effect of having a high reaction surface area and minimizing a content of a catalyst used is implemented.

The continuous stirred tank reactor for an aldol condensation reaction according to the present invention is a reactor having a bottom-up structure in which a reactant flows from a lower portion into an upper portion, and includes: a reactant inlet 100 provided in a lower portion of a reactor; a stirring unit 200 including multi-stage paddles spaced apart from each other in a vertical direction, provided in an upper side of the reactant inlet 100; and an outlet 300 provided in an upper side of the stirring unit 200, wherein the multi-stage paddles are a top pitched paddle and a plurality of multi-stage flat paddles disposed in a lower end thereof.

In the reactor, a mixture including the reactant and the catalyst flows into the reactant inlet 100 disposed in the lower portion of the reactor, the mixture is stirred and reacted while rising in a direction from the lower portion to the upper portion through the stirring unit 200, and a mixture including the reactant and a product is discharged through an outlet 300 disposed in the upper portion of the reactor, that is, the upper side of the stirring unit 200. Therefore, a volume fraction of the organic layer including the product may be maintained lower, a layer separation phenomenon may be minimized, and dead zone formation may be minimized.

Here, the stirring unit 200 is provided with a plurality of flat paddles spaced apart from each other in the lower portion of the stirring unit 200, and pitched paddles spaced apart in the upper side of the flat paddle provided in the upper portion of the stirring unit 200, that is, in the top among the plurality of flat paddles are provided in the top of the stirring unit 200. Therefore, an effect of preventing the layer separation phenomenon and dead zone formation is implemented. Up to date, layer separation and dead zone formation occurred at the top portion and at the bottom portion of the reactor, but in the present invention, the pitched paddle is disposed in the upper portion of the stirring unit 200, and a plurality of flat paddles are disposed in the lower portion of the stirring unit 200, that is, in the lower side of the pitched paddle, thereby preventing the dead zone and layer separation which may occur at the top portion of the reactor. When the pitched paddle is not provided in the upper portion, that is, at the top of the stirring unit 200, for example, the flat paddle is provided at the top of the stirring unit 200, in particular when the volume of the reactor is large, not only the layer separation phenomenon occurs even in the case in which a stirring speed is increased, but also a dead zone is formed, and rather the layer separation phenomenon may be further deteriorated by a too high stirring rate.

The reactor according to the present invention is not limited as long as it is used for the aldol condensation reaction, and as an example, the reactant to be reacted may be an aldehyde compound such as n-butyraldehyde, and in this case, the product may be an unsaturated aldehyde compound such as 2-ethylhexenal. However, it is described as only a specific and preferred example, and various kinds may be used as long as they may undergo the aldol condensation reaction, of course.

The catalyst used for reacting the reactant in the present invention is not limited as long as it may derive the aldol condensation reaction of the reactant, and as an example, both a base catalyst and an acid catalyst are usable, and for example, it may be preferred to use a base catalyst. As the base catalyst, a catalyst including any one or more selected from an aqueous NaOH solution, an aqueous KOH solution, and the like may be exemplified. However, this is described as a specific and preferred example, and the present invention is not interpreted as being necessarily limited thereto.

The continuous stirred tank reactor for an aldol condensation reaction according to a preferred exemplary embodiment may further include an impingement baffle 400 which is provided in a lower side of a bottom flat paddle among the multi-stage flat paddles and with which a reactant flowing from the inlet 100 collides to be dispersed to an outside of the reactor. As described above, the pitched paddle is provided in an upper portion of the stirring unit 200, whereby a dead zone and layer separation which may occur at the top portion of the reactor are prevented, and also, when the impingement baffle 400 is further provided, layer separation and a dead zone which may occur at the bottom of the stirring unit 200 may be prevented. More specifically, when the impingement baffle 400 is further provided in the lower portion of the reactor, that is, in the lower side of the bottom flat paddle among the plurality of flat paddles, a mixture including the reactant and the catalyst flowing from the reactant inlet 100 collides with the impingement baffle 400 and is dispersed to the outside of the reactor, that is, to the inner wall of the reactor, and simultaneously with dispersion, the mixture is stirred and reacted via the flat paddle and the pitched paddle sequentially while rising to the upper portion of the reactor. Therefore, layer separation and a dead zone which may occur at the bottom portion of the reactor may be prevented.

The impingement baffle 400 may be only formed in a structure of covering the reactant inlet 100 to be spaced apart from each other so that the mixture including the reactant and the catalyst flowing from the reactant inlet 100 collides to be dispersed in an inner wall surface direction of the reactor.

A separation distance between the impingement baffle 400 and the flat paddle and a separation distance between the impingement baffle 400 and the reactant inlet 100 may be appropriately adjusted depending on a height of a reaction space and a position of the reactant inlet 100. As a preferred example, the separation distance between the impingement baffle 400 and the flat paddle may be 4 to 26 cm, and the separation distance between the impingement baffle 400 and the reactant inlet 100 may be 2 to 26 cm, but the present invention is not limited thereto, of course.

A fixing means of the impingement baffle 400 is not limited as long as it allows the impingement baffle to be disposed to be spaced apart in the lower side of the bottom flat paddle among the flat paddles, and for example, the impingement baffle 400 may be connected to the bottom portion of the rotating shaft 240, as shown in FIG. 1, and though not shown, the impingement baffle 400 may be in contact with the inner wall surface of the reactor and fixed thereto. However, this is described as a preferred example, and the present invention is not interpreted as being necessarily limited thereto.

The stirring unit 200 may include the rotating shaft 240 connected to the multi-stage paddle. As shown in FIG. 2, a plurality of paddles are spaced apart from each other in a vertical direction and connected to the rotating shaft 240 to perform stirring by rotation.

The pitched paddle is in the form of being twisted at a determined angle in a length direction of the rotating shaft 240, as shown in FIG. 2, and the specific form and structure thereof are widely known in the art related to impellers, blades, and stirrers, the related art may be referred. As a preferred example, the pitched paddle may include a plurality of pitched blades 210 which are formed in a twisted state at an angle of 20 to 70°, specifically 30 to 60°, more specifically 35 to 55°, and as an example, at an angle of 45° in the length direction of the rotating shaft 240. Here, the number of blades may be two or more, and specifically, for example, may be 2 to 6. In addition, the twisted angle directions of the plurality of blades may be the same or different, but preferably may be the same as each other.

The flat paddle may include a plurality of flat blades 220 formed at an angle of −10 to 10° in the length direction of the rotating shaft 240, as shown in FIG. 2. Since the specific form and structure thereof are widely known in the art related to impellers, blades, and stirrers, the related art may be referred, and as a preferred example, the flat paddle may include a plurality of blades which are formed at −10 to 10°, specifically −5 to 5°, and as an example, at an angle of 0° (parallel to the length direction of the rotating shaft) in the length direction of the rotating shaft 240. Here, the number of blades may be two or more, and specifically, for example, may be 2 to 6.

The paddle may have a structure including a support 230 for connecting the pitched blade 210 or the flat blade 220 to the rotating shaft 240. The shape and structure of the support 230 are not limited as long as the support is a means for connecting and fixing the pitched blade 210 or the flat blade 220, and for example, the support 230 may have a diameter which is smaller than a length of a blade corresponding to the vertical length of the rotating shaft 240, and more preferably, may have a rod shape having a diameter of which the stirring power (lift force) is realistically negligible as compared with the blade.

As a preferred example, referring to FIG. 1, a ratio between a width (d) of the pitched blade 210 and a width (D) of the inside of the reactor is preferably 0.2 to 0.4 and a ratio between a width (d) of the flat blade 220 and the width (D) of the inside of the reactor is preferably 0.4 to 0.5. When the ratios are satisfied, an occurrence probability of the layer separation phenomenon and the dead zone may be further decreased and the effect described above may be further improved.

As a preferred example, it is preferred that the flat paddles are provided so that three or more are spaced apart from each other in the lower side of the pitched paddle, and it is more preferred that specifically 3 to 9, and more specifically 3 to 5 flat paddles are provided to be spaced apart from each other, in terms of further improving the effect described above.

A reaction area volume of the continuous stirred tank reactor according to an exemplary embodiment of the present invention is a properly adjustable matter, and as an example, the volume may be 0.6 to 1 $m^3$, but the present invention is not interpreted as being limited thereto.

A separation distance between the paddles (in the vertical direction of the rotating shaft) may be properly adjustable depending on the reactor scale, specifically the reaction area volume, and for example, may be 10 to 50 cm, based on the reaction area volume described above. In addition, the separation distance between the flat paddles (in the vertical direction of the rotating shaft) may be properly adjustable depending on the reactor scale, specifically the reaction area volume, and for example, may be 10 to 60 cm, based on the reaction area volume described above.

The reactant in the mixture including the reactant and the catalyst flowing inside through the stirring unit 200 undergoes the reaction in the form of being dispersed in the aqueous phase in a very small size, and specifically, may be dispersed in an average particle size of 50 to 500 μm, and more specifically 100 to 400 μm.

In addition, the present invention provides an apparatus for an aldol condensation reaction including the continuous stirred tank reactor for an aldol condensation reaction described above. Specifically, as shown in FIG. 3, the apparatus for an aldol condensation reaction may include the continuous stirred tank reactor 10 for an aldol condensation reaction; a plug flow reactor 20 into which a reactant, a catalyst, and a product flow from the continuous stirred tank reactor for an aldol condensation reaction; and an oil-water separator 30 into which the product and the catalyst flow from the plug flow reactor and which separates the catalyst with an aqueous layer and separates the product with an organic layer.

The apparatus for an aldol condensation reaction according to the present invention does not need to secure an additional large space as compared with a conventional apparatus, of course, even in the case of greatly increasing production so that a required output is satisfied, minimizes an average diameter of the organic layer particles dispersed in the aqueous layer during the reaction, allows the reaction state to be maintained in the entire area inside the reactor, and has not only a high reaction area and high efficiency but also may implement an effect of allowing process control of low uncertainty and a high degree of precision in spite of establishment of increased mass production system.

In the apparatus for an aldol condensation reaction according to the present invention, circulation continuously occurs in the continuous stirred tank reactor 10, the plug flow reactor 20, and the oil-water separator 30, thereby having effects that the catalyst separated as an aqueous layer in the oil-water separator 30 directly flows into the continuous stirred tank reactor 10 and is circulated, and the product may be synthesized at high conversion rate and yield, as shown in FIG. 5.

Preferably, the apparatus for an aldol condensation reaction may further include a heat exchanger 40 for transferring heat of the product to the reactant flowing into the continuous stirred tank reactor 10. Therefore, the catalyst separated as an aqueous layer in the oil-water separator 30 directly flows into the continuous stirred tank reactor 10 and is circulated, and high heat of the product is not discarded as waste heat but transferred to the reactant, thereby having an effect of synthesizing the product at a high conversion rate and a high yield even in a larger scale mass production system as compared with a conventional system.

When the catalyst separated as an aqueous layer in the oil-water separator 30 flows into the continuous stirred tank reactor 10, it is preferred that the catalyst directly flows. The fact that the catalyst separated in the oil-water separator 30 as an aqueous layer directly flows into the continuous stirred tank reactor 10 and is circulated means that the catalyst circulated through the oil-water separator 30 does not flow into the reactor via a supply line in which the reactant is transferred, but flows into the continuous stirred tank reactor 10. That is, in the present invention, the catalyst to be circulated does not flow into the supply line to be transferred to flow into the continuous stirred tank reactor 10 in a mixed state of the catalyst and the reactant. As before, when the catalyst to be circulated through the oil-water separator 30 is mixed with the reactant and then flows into the continuous stirred tank reactor 10 via a mixing supply line, particularly in the case of a mass production system having a large volume of the reaction area by a production increase, it is practically difficult to precisely control process conditions, and thus, in the entire area inside the reactor, it is difficult to maintain a reaction state in which an average diameter of organic layer particles dispersed in an aqueous layer during the reaction is minimized. This may cause decreases in the conversion rate and the yield, that is, a decrease in the output. It is preferred that the aldol condensation reaction to synthesize a product from a reactant by a catalyst occurs inside a reactor having an environment satisfying process conditions, and when the reaction occurs in the mixing supply line or the like which does not satisfy the conditions, it is difficult to control the process, uncertainty is increased, and it is difficult to have the conversion rate at or above a required level, due to an action of various variables.

The plug flow reactor (PFR) 20 may be easily designed referring to the known literature, and as an example, the inside of the reactor may be provided with spiral continuous members having constant or inconstant pitches along a length direction of a tube, but the present invention is not limited thereto, of course.

For a reaction temperature of the continuous stirred tank reactor 10 or the plug flow reactor 20, known literature may be referred, and as an example, the temperature may be 80 to 200° C., specifically 100 to 160° C. That is, the apparatus for an aldol condensation reaction according to an exemplary embodiment of the present invention may further include a temperature controller for controlling the reaction temperature of each of the reactors 10 and 20 to 50 to 150° C.

The oil-water separator 30 is a device for phase-separating an organic layer in the upper portion and an aqueous layer in the lower portion from the mixture including the catalyst and the product, and for the details thereof, the known literature may be referred. The product such as 2-ethylhexenal is present in the organic layer and the catalyst is present in the aqueous layer, and 2-ethylhexenal may be discharged through an upper pipe of the oil-water separator 30 and the catalyst may be discharged through a lower pipe of the oil-water separator 30.

The conversion rate in the continuous stirred tank reactor 10 may be preferably in a range of 30 to 60% and specifically in a range of 35 to 55%, and the conversion rate in the plug flow reactor 20 may be in a range of 95% or more, specifically 97% or more, and more specifically 97% to 99.9%. When the conversion rates in the range described above in the continuous stirred tank reactor 10 and the plug flow reactor 20 are satisfied, respectively, a final result may be a high conversion rate and a high yield of 95% or more, preferably 97% or more.

That is, the apparatus for an aldol condensation reaction according to a preferred exemplary embodiment may further include a residence time controller so that the conversion rate in the continuous stirred tank reactor 10 may be 30 to 60% and specifically 35 to 55% and the conversion rate in the plug flow reactor 20 may be 95% or more, specifically 97% or more, and more specifically 97% to 99.9%.

The residence time controller may control the residence time in the continuous stirred tank reactor 10 or the plug flow reactor 20, the residence time may be appropriately controlled so that the conversion rate described above is satisfied, and for example, the residence time may be controlled to 1 second to 10 minutes, specifically 10 seconds to 5 minutes. However, this is described as a preferred example, and the present invention is not interpreted as being necessarily limited thereto.

For a reaction pressure of the continuous stirred tank reactor 10 or the plug flow reactor 20, known literature may be referred, and as an example, the pressure may be in a range of 1 to 50 bar and specifically 2 to 10 bar. That is, the apparatus for an aldol condensation reaction according to an exemplary embodiment of the present invention may further include a pressure controller for controlling the pressure of each of the reactors 10 and 20 to the above range.

In the present invention, the reactant is reacted in a liquid phase by the catalyst to synthesize a product, the reaction occurs in a liquid phase, and a solution including the reactant, the catalyst, and/or the product may be transferred by a pump 50. A position of the pump 50 is not largely limited, and as an example, may be provided between the continuous stirred tank reactor 10 and the plug flow reactor 20. However, this is described as a specific example, and the present invention is not interpreted as being necessarily limited thereto.

In the continuous stirred tank reactor 10 or the plug flow reactor 20, for a flow rate of the solution including the reactant, the catalyst, and/or the product, known literature may be referred, and as an example, the flow rate may be in a volume flow rate range of 50 to 200 m³/hr. That is, the apparatus for an aldol condensation reaction according to an exemplary embodiment of the present invention may further include a flow rate controller for controlling the flow rate of the solution in each of the reactors 10 and 20 to the above range.

The invention claimed is:

1. A continuous stirred tank reactor for an aldol condensation reaction having a bottom-up structure in which a reactant flows from a lower portion into an upper portion, the continuous stirred tank reactor comprising:
    a reactant inlet 100 provided in a lower portion of the reactor;
    a stirring unit 200 including multi-stage paddles spaced apart from each other in a vertical direction, provided in an upper side of the reactant inlet 100; and
    an outlet 300 provided in an upper side of the stirring unit 200,
    wherein the multi-stage paddles are a pitched paddle disposed at a top and a plurality of multi-stage flat paddles disposed in a lower end thereof.

2. The continuous stirred tank reactor for an aldol condensation reaction of claim 1, wherein
    the stirring unit 200 includes a rotating shaft 240 connected to the multi-stage paddle; and
    the pitched paddle includes a plurality of pitched blades 210 formed in a state of being twisted at an angle of 20 to 70° in a length direction of the rotating shaft 240.

3. The continuous stirred tank reactor for an aldol condensation reaction of claim 1, wherein
    the stirring unit 200 includes the rotating shaft 240 connected to the multi-stage paddle; and
    the flat paddle includes a plurality of flat blades 220 formed at an angle of −10 to 10° in the length direction of the rotating shaft 240.

4. The continuous stirred tank reactor for an aldol condensation reaction of claim 1, further comprising an impingement baffle 400 which is provided in a lower side of a bottom flat paddle among the multi-stage flat paddles and with which a reactant flowing from the inlet 100 collides to be dispersed to an outside of the reactor.

5. The continuous stirred tank reactor for an aldol condensation reaction of claim 1, wherein
    the paddle includes a support 230 for connecting the pitched blade 210 to the rotating shaft 240, and
    a ratio between a width (d) of the pitched blade 210 and a width (D) of an inside of the reactor is 0.2 to 0.4.

6. The continuous stirred tank reactor for an aldol condensation reaction of claim 1, wherein
    the paddle includes a support 230 for connecting the pitched blade 210 to the rotating shaft 240, and
    a ratio between a width (d) of the flat blade 220 and a width (D) of the inside of the reactor is 0.4 to 0.5.

7. The continuous stirred tank reactor for an aldol condensation reaction of claim 1, wherein
    the stirring unit 200 allows the reactant to be dispersed in an aqueous phase at an average particle size of 50 to 500 μm.

8. An apparatus for an aldol condensation reaction comprising the continuous stirred tank reactor for an aldol condensation reaction of claim 1.

9. The apparatus for an aldol condensation reaction of claim 8, comprising:
    the continuous stirred tank reactor 10 for an aldol condensation reaction;
    a plug flow reactor 20 into which a reactant, a catalyst, and a product flow from the continuous stirred tank reactor for an aldol condensation reaction; and
    an oil-water separator 30 into which the product and the catalyst flow from the plug flow reactor and which separates the catalyst with an aqueous layer and separates the product with an organic layer.

* * * * *